US012697018B2

(12) United States Patent
Watanabe

(10) Patent No.: US 12,697,018 B2
(45) Date of Patent: Aug. 4, 2026

(54) INSERTION DEVICE

(71) Applicant: OLYMPUS CORPORATION, Tokyo (JP)

(72) Inventor: Tadashi Watanabe, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 448 days.

(21) Appl. No.: 18/219,789

(22) Filed: Jul. 10, 2023

(65) Prior Publication Data

US 2023/0346209 A1 Nov. 2, 2023

Related U.S. Application Data

(63) Continuation of application No. PCT/JP2021/007400, filed on Feb. 26, 2021.

(51) Int. Cl.
*A61B 1/06* (2006.01)

(52) U.S. Cl.
CPC .......... *A61B 1/0676* (2013.01); *A61B 1/0646* (2013.01)

(58) Field of Classification Search
CPC ............ A61B 1/00013; A61B 1/00016; A61B 1/00165; A61B 1/00167; A61B 1/0017; A61B 1/05; A61B 1/051; A61B 1/053
See application file for complete search history.

(56) References Cited

U.S. PATENT DOCUMENTS

2013/0012777 A1* 1/2013 Baum ................ A61B 1/00165
600/110
2016/0262599 A1* 9/2016 Nakagawa ........... A61B 1/0057

2017/0078583 A1 3/2017 Haggerty et al.
2018/0136456 A1 5/2018 Watanabe et al.
2020/0196832 A1* 6/2020 Urakawa ................ A61B 1/051
2021/0068617 A1* 3/2021 Liou .................... H05K 1/0243
(Continued)

FOREIGN PATENT DOCUMENTS

JP S61-121590 A 6/1986
JP 2017217080 A * 12/2017
(Continued)

OTHER PUBLICATIONS

International Search Report dated Apr. 20, 2021 received in PCT/JP2021/007400.

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

An insertion device includes: an insertion portion configured to be inserted into a subject; an imaging unit that includes an imaging element and an optical element and that is arranged at a distal end of the insertion portion, the imaging unit being configured to capture an internal image of the subject to generate an image signal; a transmitter that is arranged adjacent to a proximal end side of the imaging unit in the insertion portion, the transmitter being configured to transmit the image signal using millimeter waves or submillimeter waves; and a waveguide that is arranged on a proximal end side of the transmitter in the insertion portion and at a position distant from the transmitter with a distal end surface of the waveguide facing the transmitter, the waveguide being configured to propagate the millimeter waves or submillimeter waves.

6 Claims, 9 Drawing Sheets

(56) References Cited

U.S. PATENT DOCUMENTS

2022/0046205 A1      2/2022   Watanabe
2024/0000294 A1*    1/2024   Rauscher  ........... A61B 1/00193

FOREIGN PATENT DOCUMENTS

JP           2020-137072 A        8/2020
WO           2017/002585 A1       1/2017
WO      WO-2018203452 A1  *  11/2018   ............. A61B 1/051

* cited by examiner

INSERTION DEVICE

CROSS-REFERENCE TO RELATED APPLICATION

This application is a continuation of International Application No. PCT/JP2021/007400, filed on Feb. 26, 2021, the entire contents of which are incorporated herein by reference.

BACKGROUND

1. Technical Field

The present disclosure relates to an insertion device.

2. Related Art

An endoscope system including an endoscope that includes an insertion portion having a distal end in which an imaging unit is provided and that is inserted into a subject and a control device that processes an image signal from the imaging unit has been known (refer to Japanese Laid-open Patent Publication No. 61-121590).

In the endoscope system described in Japanese Laid-open Patent Publication No. 61-121590, the imaging unit and the control device are connected with a lead wire and the image signal from the imaging unit is transferred to the control device via the lead wire.

FIG. 10 is a diagram for describing a conventional problem. Specifically, FIG. 10 shows a relationship between a transfer distance over which transmission by an electric interconnection (lead wire connection) is possible and a transfer rate.

In the endoscope system described in Japanese Laid-open Patent Publication No. 61-121590, the imaging unit and the control device are connected with the lead wire and thus, when a length of a transfer path is about 1 to 2 m, the limit of the transfer rate is about 2.5 Gbps. Moreover, a connection portion between the imaging unit and the lead wire prevents a diameter of the distal end portion of the insertion portion from reducing.

SUMMARY

In some embodiments, an insertion device includes: an insertion portion configured to be inserted into a subject; an imaging unit that includes an imaging element and an optical element and that is arranged at a distal end of the insertion portion, the imaging unit being configured to capture an internal image of the subject to generate an image signal; a transmitter that is arranged adjacent to a proximal end side of the imaging unit in the insertion portion, the transmitter being configured to transmit the image signal using millimeter waves or submillimeter waves; and a waveguide that is arranged on a proximal end side of the transmitter in the insertion portion and at a position distant from the transmitter with a distal end surface of the waveguide facing the transmitter, the waveguide being configured to propagate the millimeter waves or submillimeter waves.

In some embodiments, an insertion device includes: an insertion portion configured to be inserted into a subject; a distal end unit that is arranged at a distal end of the insertion portion; a displacement portion that is arranged on a proximal end side of the distal end unit in the insertion portion, the displacement portion being configured to displace the distal end unit with respect to a longitudinal axis of the insertion portion; a flexible tube that is arranged on a proximal end side of the displacement portion in the insertion portion; an imaging unit that includes an imaging element and an optical element and that is arranged in the distal end unit, the imaging unit being configured to capture an internal image of the subject to generate an image signal; a transmitter that is arranged adjacent to a proximal end side of the imaging unit in the distal end unit, the transmitter being configured to transmit the image signal using millimeter waves or submillimeter waves; and a flexible waveguide that is inserted into the flexible tube, the flexible waveguide being configured to propagate the millimeter waves or submillimeter waves with the displacement portion being interposed between the flexible waveguide and the distal end unit and with a distal end surface of the flexible waveguide facing the transmitter.

In some embodiments, an insertion device includes: an insertion portion configured to be inserted into a subject; an imaging unit that includes an imaging element and an optical element and that is arranged outside on a distal end side of the insertion portion with respect to a distal end of the insertion portion such that the imaging unit can be displaced with respect to the distal end of the insertion portion, the imaging unit being configured to capture an internal image of the subject to generates an image signal; a transmitter that is arranged adjacent to a proximal end side of the imaging unit, the transmitter being configured to transmit the image signal using millimeter waves or submillimeter waves; and a waveguide that is arranged at a distal end portion of the insertion portion with a distal end surface of the waveguide facing the transmitter, the waveguide being configured to propagate the millimeter waves or submillimeter waves.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
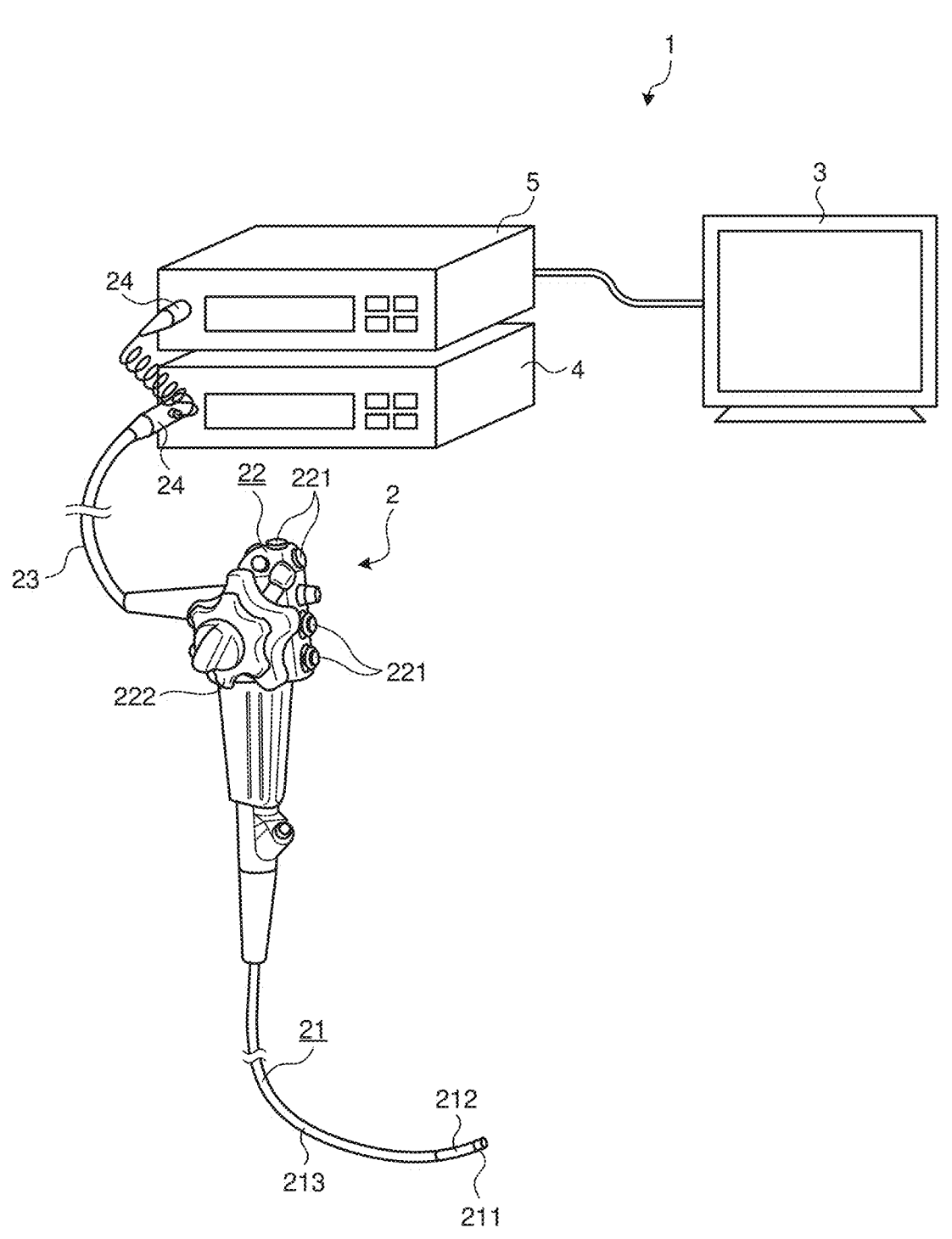
FIG. 1 is a diagram illustrating a configuration of an endoscope system according to a first embodiment.

With reference to the accompanying drawings, modes for carrying out the disclosure ("embodiments" below) will be described below. Note that the embodiments described below do not limit the disclosure. Furthermore, in the illustration of the drawings, the same parts are denoted with the same reference numerals.

First Embodiment

Configuration of Endoscope System

Figure 2:
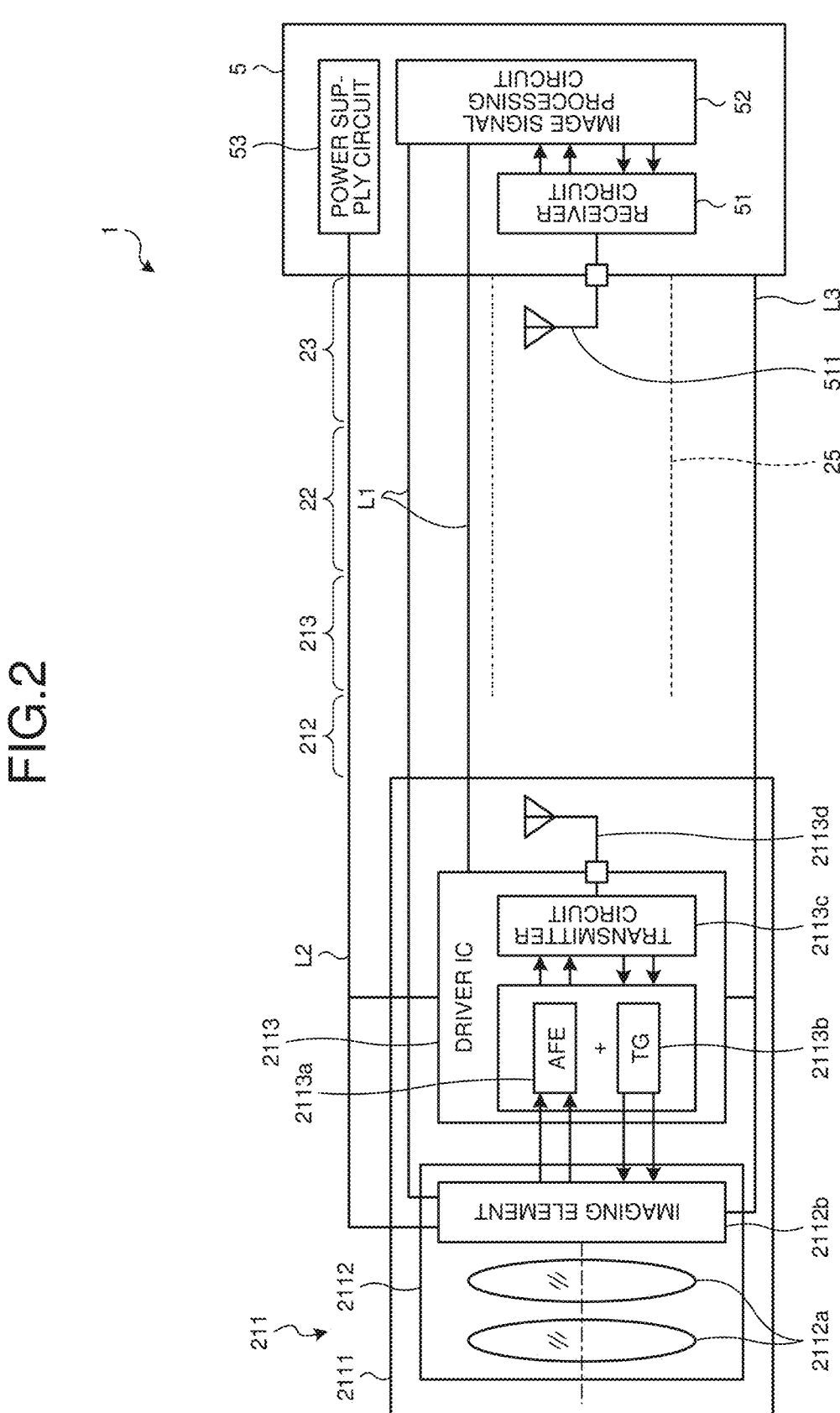
FIG. 2 is a diagram illustrating a configuration of a relevant part of the endoscope system.

FIG. 1 is a diagram illustrating a configuration of an endoscope system 1 according to a first embodiment. FIG. 2 is a diagram illustrating a configuration of a relevant part of the endoscope system 1.

The endoscope system 1 is a system that is used in, for example, the medical fields and that observes the inside of a subject (the inside of a living body). As illustrated in FIG. 1 or FIG. 2, the endoscope system 1 includes an endoscope 2, a display device 3 (FIG. 1), a light source device 4 (FIG. 1), and a control device 5.

The endoscope 2 corresponds to an insertion device. The endoscope 2 is partly inserted into a living body, captures a subject image that is reflected from the inside of the living body, and outputs an image signal that is generated by the image capturing. As illustrated in FIG. 1, the endoscope 2 includes an insertion portion 21, an operation portion 22, a universal cord 23, a connector 24, and a waveguide 25 (refer to FIG. 2).

The insertion portion 21 is a part that is at least partly flexible and that is inserted into the living body. As illustrated in FIG. 1 or FIG. 2, the insertion portion 21 includes a distal end unit 211, a bendable portion 212, and a flexible tube 213.

The distal end unit 211 is arranged at a distal end of the insertion portion 21. As illustrated in FIG. 2, the distal end unit 211 includes a distal end rigid portion 2111, an illumination optical system (not illustrated in the drawings), an imaging unit 2112, and a driver integrated circuit (IC) 2113.

The distal end rigid portion 2111 is, for example, a rigid member that is formed of a resin material.

The illumination optical system is supported on the distal end rigid portion 2111. The illumination optical system faces one end of a light guide (not illustrated in the drawing) that is drawn in the insertion portion 21 and applies light that is transmitted by the light guide to the inside of the living body from the distal end of the insertion portion 21.

The imaging unit 2112 is supported on the distal end rigid portion 2111. The imaging unit 2112 includes an imaging optical system 2112a and an imaging element 2112b.

The imaging optical system 2112a corresponds to an optical element. The imaging optical system 2112a guides the light (the subject image) that is applied from the illumination optical system and that is reflected from the inside of the living body and forms an image on an imaging surface of the imaging element 2112b.

The imaging element 2112b is an imaging element, such as a charge coupled device (CCD) or a complementary metal oxide semiconductor (CMOS), captures the subject image that is formed by the imaging optical system 2112a, and outputs the image signal that is generated by the image capturing.

As illustrated in FIG. 2, a control signal line L1 that transfers a control signal that is output from the control device 5 toward the imaging element 2112b, a power line L2 that transfers power that is supplied from the control device 5 to the imaging element 2112b, and a ground line L3 are connected to the imaging element 2112b.

The driver IC 2113 is a part that is arranged in a state of being adjacent to a proximal end side of the imaging unit

2112 and that, under the control of the control device 5, drives the imaging element 2112b and transmits the image signal that is output from the imaging element 2112b. As illustrated in FIG. 2, the driver IC 2113 includes an analog front end (AFE) 2113a, a timing generator (TG) 2113b, and a transmitter circuit 2113c.

The AFE 2113a performs denoising and A/D conversion on the image signal (analog signal) that is output from the imaging element 2112b.

The TG 2113b generates timings for driving the imaging element 2112b and pulses for various types of signal processing in the AFE 2113a, etc.

The transmitter circuit 2113c corresponds to a transmitter. The transmitter circuit 2113c is a communication circuit that is formed using, for example, a monolithic microwave integrated circuit (MMIC) and that uses millimeter waves or submillimeter waves ("millimeter waves/submillimeter waves" below) and performs communication with the control device 5. Specifically, using millimeter waves/submillimeter waves, the transmitter circuit 2113c transmits the image signal, which is output from the AFE 2113a, from an antenna 2113d that is connected to the transmitter circuit 2113c. The millimeter waves/submillimeter waves that are transmitted from the transmitter circuit 2113c (the antenna 2113d) are propagated by the waveguide 25 to the control device 5. The millimeter waves are radio waves having a wavelength of approximately 1 to 10 mmm and the submillimeter waves are radio waves having a wavelength of approximately 0.1 to 1 mmm.

As illustrated in FIG. 2, the control signal line L1 that transfers the control signal that is output from the control device 5 toward the driver IC 2113, the power line L2 that transfers power that is supplied form the control device 5 to the driver IC 2113, and the ground line L3 are connected to the driver IC 2113.

The bendable portion 212 is coupled to a proximal end side (the side of the operation portion 22) of the distal end unit 211. In other words, the distal end unit 211 is provided on the distal end side of the bendable portion 212. The bendable portion 212 has a configuration in which, although not specifically illustrated in the drawings, a plurality of bending pieces are coupled such that the bendable portion 212 is bendable.

The flexible tube 213 is coupled to a proximal end side (the side of the operation portion 22) of the bendable portion 212 and has an elongated form that is flexible.

The operation portion 22 is connected to a proximal end portion of the insertion portion 21. The operation portion 22 receives various types of operations on the endoscope 2. As illustrated in FIG. 1 or FIG. 2, the operation portion 22 is provided with a plurality of operation parts 221 and a knob 222.

The operation parts 221 consist of buttons that receive various types of operations, or the like.

The knob 222 is configured to be rotatable according to a user operation. A rotation of the knob 222 causes a bendable mechanism (not illustrated in the drawings), such as a wire that is arranged in the insertion portion 21 and that is made of metal or resin, to operate. Accordingly, this operation bends the bendable portion 212.

The universal cord 23 is a cord that extends from the operation portion 22 in a direction different from the direction in which the insertion portion 21 extends and, in the universal cord 23, the above-described light guide, the waveguide 25, the control signal line L1, the power line L2, and the ground line L3, etc., are arranged.

The connector 24 is provide at an end of the universal cord 23 and is detachably connected to the light source device 4 and the control device 5.

The waveguide 25 is a waveguide that is flexible and elongated and that propagates millimeter waves/submillimeter waves from one end to the other end. In other words, the waveguide 25 corresponds to a flexible waveguide in addition to a waveguide specific to the invention. As illustrated in FIG. 2, the waveguide 25 includes a core 251 and an outer conductor 252.

The core 251 is made of a rod-shaped dielectric that is extended in a state such that the permittivity is constant in a longitudinal direction of the waveguide 25.

The outer conductor 252 is provided on an outer circumference of the core 251 and that is formed by braiding filament yarns into a braid.

Note that the position of arrangement of the waveguide 25 will be described in "Position of Arrangement of Waveguide" described below.

The display device 3 is a device, such as a liquid crystal display (LCD) or an electro luminescence (EL) display, and displays a given image under the control of the control device 5.

The light source device 4 emits illumination light. The illumination light that is emitted from the light source device 4 to the inside of the body from the distal end of the insertion portion 21 via the connector 24, the universal cord 23, the operation portion 22, the aforementioned light guide that is drawn in the insertion portion 21, and the illumination optical system.

The control device 5 is configured by including a central processing unit (CPU), a field-programmable gate array (FPGA), or the like, and generally controls operations of the display device 3 and the light source device 4. As illustrated in FIG. 2, the control device 5 includes a receiver circuit 51, an image signal processing circuit 52, and a power supply circuit 53.

Like the transmitter circuit 2113c, the receiver circuit 51 is a communication circuit that is formed using, for example, a MMIC and that uses millimeter waves/submillimeter waves and performs communication with the transmitter circuit 2113c via an antenna 511. In other words, the receiver circuit 51 receives, via the antenna 511, the image signal on the millimeter waves/submillimeter waves that are transmitted from the transmitter circuit 2113c (the antenna 2113d) and that are propagated by the waveguide 25. The receiver circuit 51 then outputs the received image signal to the image signal processing circuit 52.

The image signal processing circuit 52 generates an endoscopic image by performing given processing on the image signal output from the receiver circuit 51. The image signal processing circuit 52 controls operations of the display device 3 and causes the display device 3 to display the endoscopic image, etc.

The image signal processing circuit 52 generates control signals (for example, clock signals, synchronization signals, or the like) for controlling the imaging element 2112b and the driver IC 2113 and outputs the control signals to the imaging element 2112b and the driver IC 2113 via the control signal line L1.

The power supply circuit 53 generates a power for driving the imaging element 2112b and the driver IC 2113 and supplies the power to the imaging element 2112b and the driver IC 2113 via the power line L2 and the ground line L3. Note that, in the first embodiment, the light source device 4 and the control device 5 are configured independently; however, the light source device 4 and the control device 5 may be provided integrally in a single casing.

Position of Arrangement of Waveguide

Figure 3:
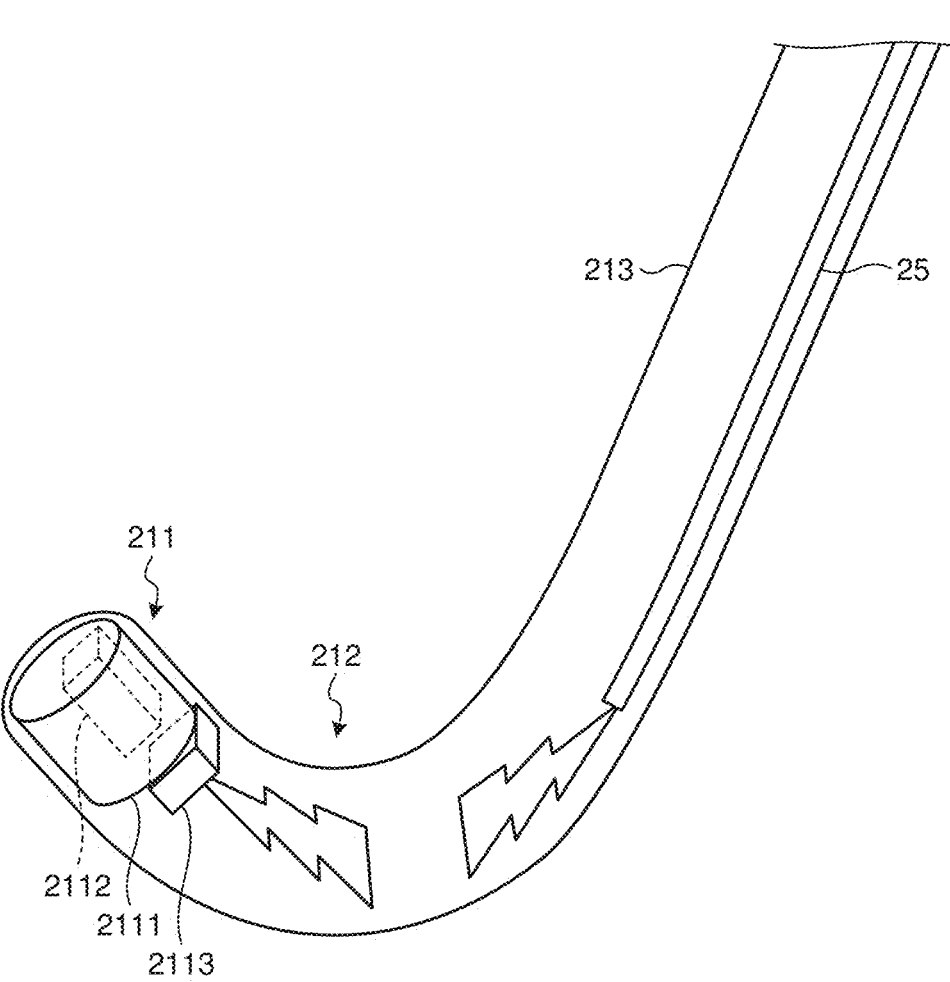
FIG. 3 is a diagram for describing a position of arrangement of a flexible waveguide.

FIG. 3 is a diagram for describing a position of arrangement of the waveguide 25.

As illustrated in FIG. 2, one end of the waveguide 25 is positioned in the connector 24. When the connector 24 is attached to the control device 5, the one end of the waveguide 25 faces the antenna 511.

The waveguide 25 is arranged on the proximal end side of the distal end unit 211 and in a position distant from the transmitter circuit 2113c with the other end of the waveguide 25 facing the transmitter circuit 2113c. In the first embodiment, the waveguide 25 is drawn in the endoscope 2 to a position on the proximal end side of the bendable portion 212 through a path from the connector 24 to the flexible tube 213 via the universal cord 23 and the operation portion 22. As illustrated in FIG. 2 or FIG. 3, the other end of the waveguide 25 is fixed in the flexible tube 213. Thus, the millimeter waves/submillimeter waves that are transmitted from the transmitter circuit 2113c (the antenna 2113d) are introduced via a transfer path consisting of the air in the bendable portion 212 into the waveguide 25 from the other end of the waveguide 25 and are propagated by the waveguide 25 to the receiver circuit 51 (the antenna 511).

The above-described transfer path in the bendable portion 212 may consist of the air without anything placed as described above or may consist of a dielectric that is put in the bendable portion 212.

According to the first embodiment described above, the following effect is achieved.

The endoscope 2 according to the first embodiment transmits an image signal from the distal end unit 211 using millimeter waves/submillimeter waves and propagates the millimeter waves/submillimeter waves using the waveguide 25 that is arranged in the position distant from the distal end unit 211.

In other words, using the millimeter waves/submillimeter waves and the waveguide 25 makes it possible to overcome the limit of the transfer rate in the case where a conventional transfer path is a lead wire. Furthermore, joining the distal end unit 211 and the waveguide 25 is unnecessary and therefore it is possible to minimize the joint to the distal end unit 211 and reduce the diameter of the distal end portion of the insertion portion 21.

Particularly, the waveguide 25 is flexible and is inserted into the flexible tube 213. The waveguide 25 is appropriately sagged together with the flexible tube 213. In other words, even when the waveguide 25 is installed, usability of the insertion portion 21 is not impaired.

The waveguide 25 is provided on the proximal end side of the bendable portion 212. In other words, nothing is provided in the bendable portion 212. For this reason, even when the waveguide 25 is installed, it is possible to bend the bendable portion 212 smoothly. Fixing the distal end side of the waveguide 25 to a ferrule (not illustrated in the drawings) for connecting, for example, the proximal end side of the bendable portion 212 and the flexible tube 213 stabilizes the distal end position of the waveguide 25 in the insertion portion 21.

Second Embodiment

A second embodiment will be described next.

In the following description, the same components as those of the above-described first embodiment are denoted with the same reference numerals as those of the first embodiment and detailed description thereof will be omitted or simplified.

Figure 4:
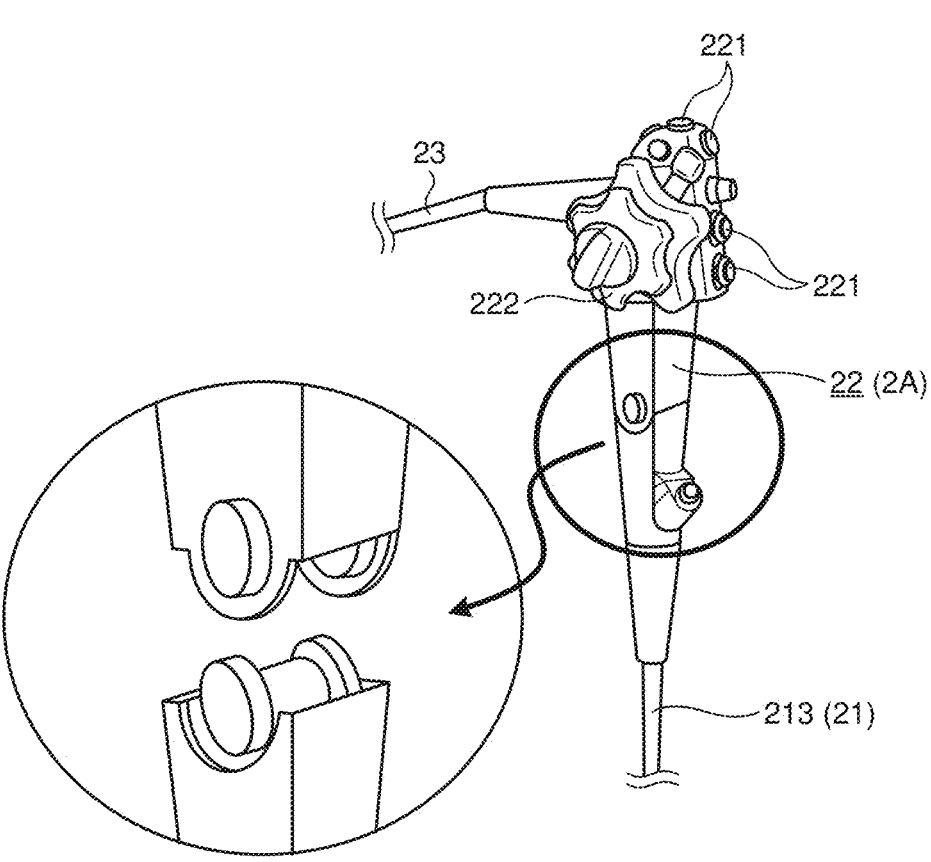
FIG. 4 is a diagram illustrating an endoscope according to a second embodiment.

FIG. 4 is a diagram illustrating an endoscope 2A according to the second embodiment.

In the endoscope 2A according to the second embodiment, as illustrated in FIG. 4, the operation portion 22 is configured such that the operation portion 22 is dividable into two parts on the side of the insertion portion 21 and the side of the universal cord 23. Although not specifically illustrated in the drawings, the light guide, the waveguide 25, the control signal line L1, the power line L2, and the ground line L3 that are described above are configured such that each of them is dividable into two parts via a connector in the position of division in the operation portion 22 described above.

According to the second embodiment described above, in addition to the same effects as those of the first embodiment described above, the following effect is achieved.

In the endoscope 2A according to the second embodiment, the operation portion 22 is dividable into the two parts on the side of the insertion portion 21 and the side of the universal cord 23. For thig reason, in the endoscope 2A, one of the two divided parts on the side of the universal cord 23 serves as a reuse part and the other part on the side of the insertion portion 21 serves as a single use.

Third Embodiment

A third embodiment will be described next.

In the following description, the same components as those of the above-described first embodiment are denoted with the same reference numerals as those of the first embodiment and detailed description thereof will be omitted or simplified.

Figure 5:
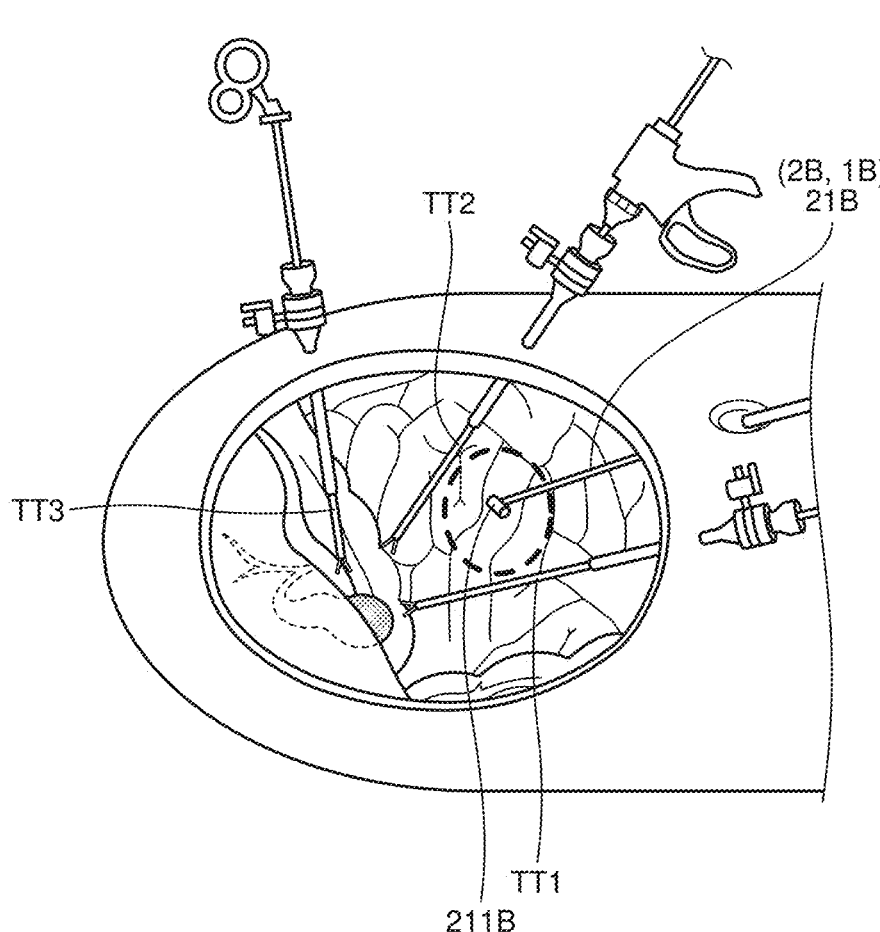
FIG. 5 is a diagram illustrating a configuration of a relevant part of an endoscope system according to a third embodiment.
Figure 6:
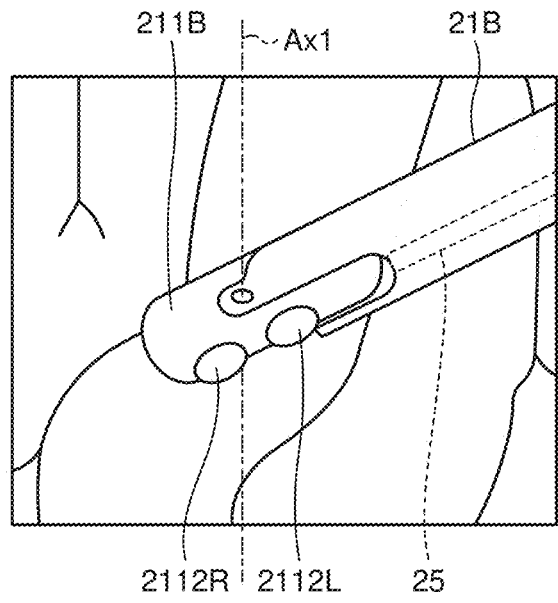
FIG. 6 is a diagram illustrating the configuration of the relevant part of the endoscope system according to the third embodiment.
Figure 7:
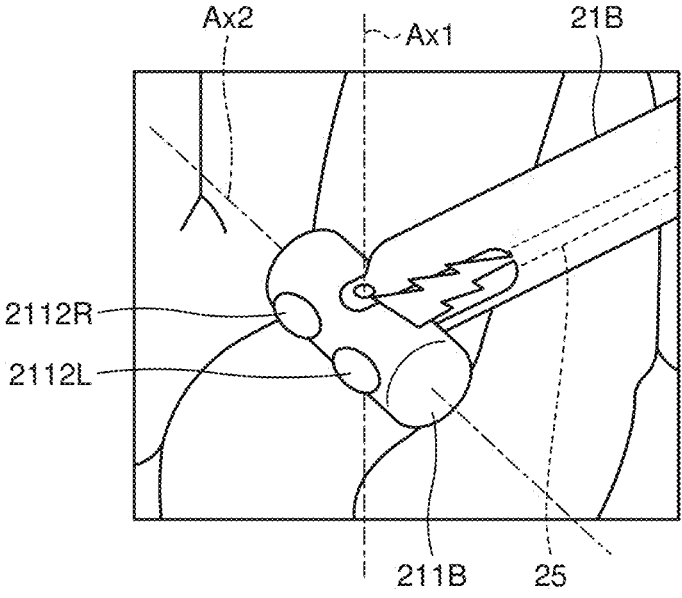
FIG. 7 is a diagram illustrating the configuration of the relevant part of the endoscope system according to the third embodiment.
Figure 8:
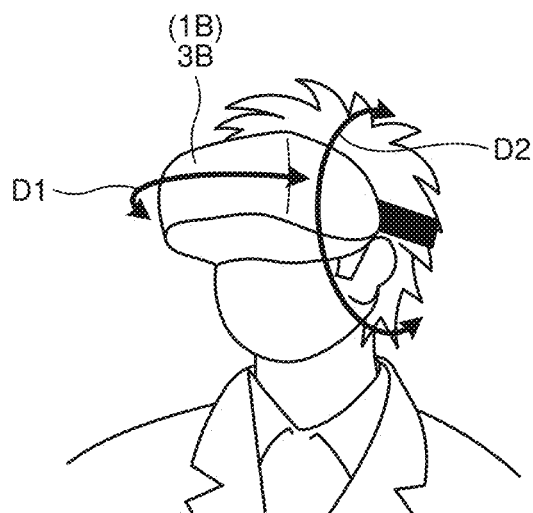
FIG. 8 is a diagram illustrating the configuration of the relevant part of the endoscope system according to the third embodiment.

FIGS. 5 to 8 are diagrams illustrating a configuration of a relevant part of an endoscope system 1B according to a third embodiment. Specifically, FIG. 5 is a diagram illustrating the inside of an abdominal cavity during a laparoscopic surgery. According to FIG. 5, in addition to an insertion portion 21B of an endoscope 2B constituting the endoscope system 1B, each of distal end portions of three treatment tools TT1 to TT3 is inserted into the abdominal cavity. FIGS. 6 and 7 are diagrams illustrating a distal end portion (the portion indicated by the dashed circle in FIG. 5) of the insertion portion 21B in the endoscope 2B constituting the endoscope system 1B. FIG. 8 is a diagram illustrating a display device 3B constituting the endoscope system 1B.

In the endoscope system 1B according to the third embodiment, as illustrated in FIGS. 5 to 8, the following changes are made to the endoscope system 1 described in the above-described first embodiment.

In other words, as illustrated in FIGS. 5 to 7, the endoscope system 1B employs the endoscope 2B on which a distal end unit 211B that is configured differently from the distal end unit 211 is mounted instead of the endoscope 2 described in the above-described first embodiment.

As illustrated in FIG. 8, the endoscope system 1B employs the display device 3B consisting of a head-up display instead of the display device 3 described in the above-described first embodiment.

The distal end unit 211B is arranged at the distal end of the insertion portion 21. In the second embodiment, as illustrated in FIG. 6 or FIG. 7, the distal end unit 211B is arranged outside further on the distal end side with respect to the distal end of the insertion portion 21.

The distal end unit 211B has approximately the same configuration as that of the distal end unit 211 described in the above-described first embodiment and is different from the distal end unit 211 in having a stereo camera function. In other words, as illustrated in FIG. 6 or FIG. 7, the distal end unit 211B employs a left-eye imaging unit 2112L and a right-eye imaging unit 2112R instead of the imaging unit 2112 described in the above-described first embodiment. Although not specifically illustrated in the drawings, the configurations of the left-eye imaging unit 2112L and the right-eye imaging unit 2112R are the same as that of the imaging unit 2112. The left-eye imaging unit 2112L and the right-eye imaging unit 2112R are arranged in parallel in a longitudinal direction of the distal end unit 211B. The left-eye imaging unit 2112L and the right-eye imaging unit 2112R generate a left-eye image signal (left-eye image) and a right-eye image signal (right-eye image) with a disparity therebetween, respectively.

Although not specifically illustrated in the drawings, the distal end unit 211B employs driver ICs corresponding to the left-eye imaging unit 2112L and the right-eye imaging unit 2112R, respectively, instead of the driver IC 2113 described in the above-described first embodiment. Note that the distal end unit 211B is provided with only a single transmitter circuit.

In the distal end unit 211B, using millimeter waves/submillimeter waves, the transmitter circuit transmits the left and right image signals that are respectively output from AFEs constituting the respective driver ICs from an antenna that is connected to the transmitter circuit. As in the case of the above-described first embodiment, the millimeter waves/submillimeter waves are propagated by the waveguide 25 to the control device 5. After receiving the left and right image signals on the millimeter waves/submillimeter waves, the control device 5 generates, for example, a three-dimensional video signal according to the side-by-side method, or the like, from the left image based on the left image signal and the right image based on the right image signal and outputs the three-dimensional video signal to the display device 3B. The display device 3B then makes a 3D display of the left-eye image and the right-eye image based on the three-dimensional video signal.

Displacing the distal end unit 211B described above with respect to the distal end of the insertion portion 21 makes it possible to change an imaging field. Specifically, the distal end unit 211B is capable of changing the imaging field by rotating on a rotation axis Ax1 (FIG. 6 and FIG. 7) orthogonal to a longitudinal direction of the insertion portion 21. For example, the distal end unit 211B rotates on the rotation axis Ax1 according to a user operation on the operation part 221. For example, when the insertion portion 21 is inserted into a living body, the distal end unit 211B rotates on the rotation axis Ax1 according to the user operation and thus is set in a posture such that the longitudinal direction of the distal end unit 211B is approximately the same direction as the longitudinal direction of the insertion portion 21.

Although not specifically illustrated in the drawings, the display device 3B is provided with a detection sensor, such as a gyro sensor, that detects a posture of the display device 3B. The detection sensor outputs a signal representing the detected posture of the display device 3B to the control device 5. Based on the signal that is output from the detection sensor, the control device 5 causes the distal end unit 211B to rotate on the rotation axis Ax1. When the display device 3B rotates in a direction D1 represented by the arrow illustrated in FIG. 8, the distal end unit 211B rotates on the rotation axis Ax1 in association with the rotation in the direction D1.

In addition to the rotation axis Ax1, a rotation axis Ax2 may be set as the rotation axis of the distal end unit 211B. The rotation axis Ax2 is an axis orthogonal to each of the longitudinal direction of the insertion portion 21 and the rotation axis Ax1. Based on the signal that is output from the detection sensor described above, the control device 5 causes the distal end unit 211B to rotate on each of the rotation axes Ax1 and Ax2. Accordingly, the distal end unit 211B rotates on the rotation axis Ax1 in association with the rotation of the display device 3B in the direction D1 represented by the arrow illustrated in FIG. 8 and rotates on the rotation axis Ax2 in association with a rotation of the display device 3B in a direction D2 represented by an arrow D2 illustrated in FIG. 8.

According to the third embodiment described above, the following effect is achieved in addition to the same effect as that of the above-described first embodiment.

In the endoscope 2B according to the third embodiment, the distal end unit 211B is arranged outside further on the distal end side with respect to the distal end of the insertion portion 21 and is displaced with respect to the distal end of the insertion portion 21 and thus the imaging filed is changeable.

For this reason, changing the imaging field makes it possible to increase the area that can be observed and increase usability.

Particularly, the distal end unit 211B is provided with the left-eye and right-eye imaging units 2112L and 2112R. The control device 5 makes a 3D display of the left and right images that are captured by the left-eye and right-eye imaging units 2112L and 2112R on the display device 3B. This enables the user to observe an image of an affected site as a stereoscopic three-dimensional image.

Modification 3-1 of Third Embodiment

Figure 9:
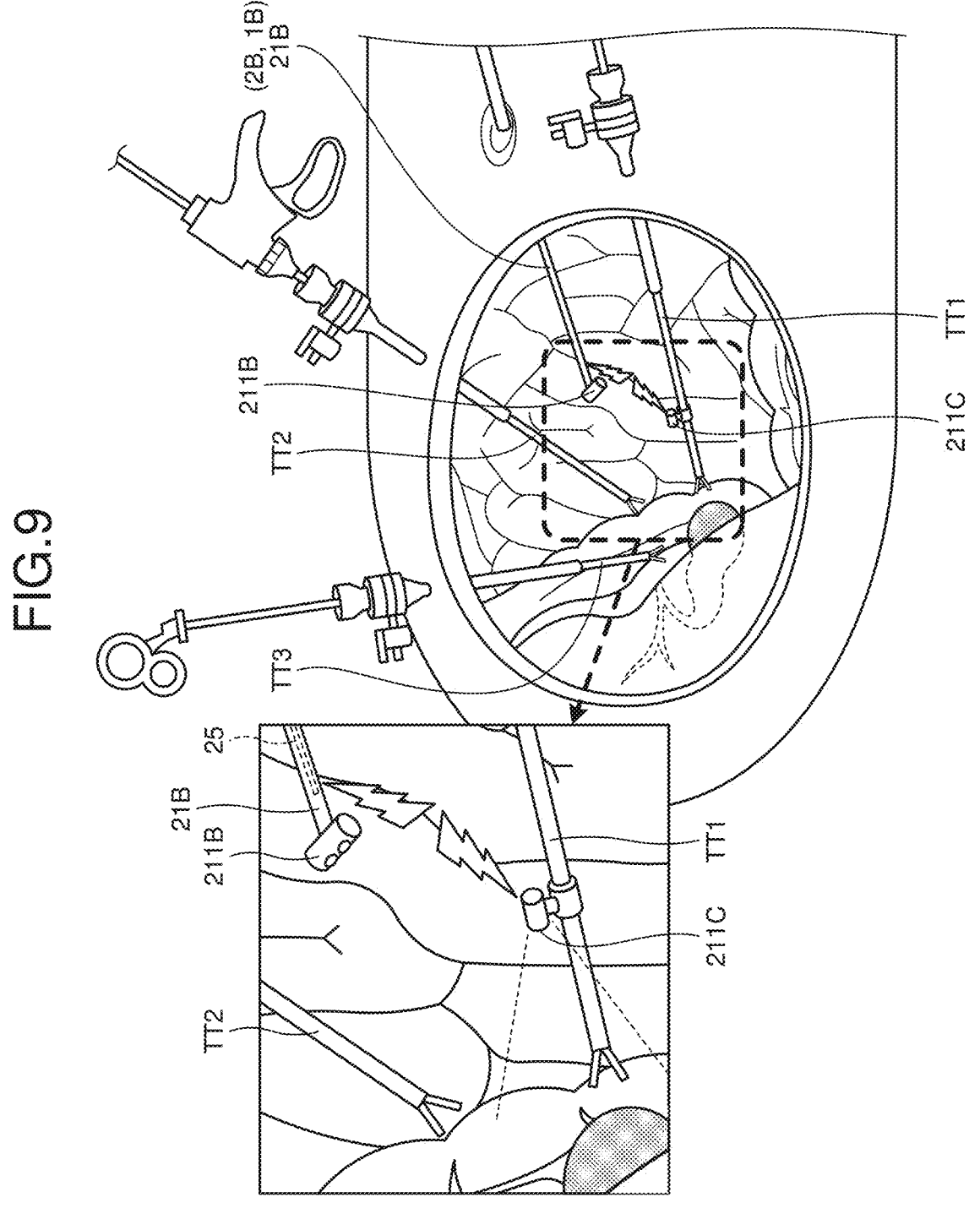
FIG. 9 is a diagram illustrating a modification of the third embodiment.
Figure 10:
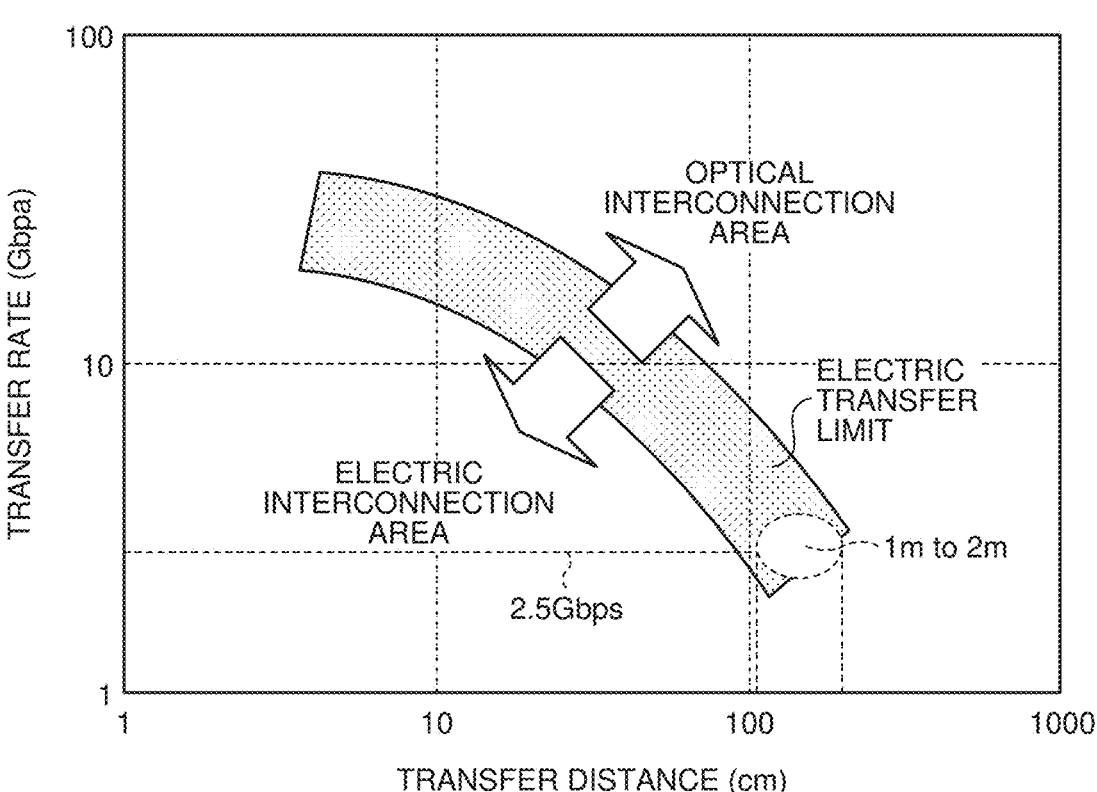
FIG. 10 is a diagram for describing a conventional problem.

FIG. 9 is a diagram illustrating a modification of the third embodiment. Specifically, FIG. 9 is a diagram corresponding to FIG. 5.

In the above-described third embodiment, as illustrated in FIG. 9, an auxiliary camera 211C may be attached to at least any one of the three treatment tools TT1 to TT3. FIG. 9 illustrates the state where the auxiliary camera 211C is attached to the treatment tool TT1.

The auxiliary camera 211C is configured to include "a transmitter with which another insertion device is provided". Although not specifically illustrated in the drawings, the auxiliary camera 211C has the same configuration as that of the distal end unit 211 described in the above-described first embodiment. The auxiliary camera 211C generates an image signal by capturing an image using, as the imaging field, the distal end portion of the treatment tool TT1 to which the auxiliary camera 211C is attached. The auxiliary camera 211C transmits the image signal using millimeter waves/ submillimeter waves.

The waveguide 25 that is provided in the endoscope 2B guides the millimeter waves/submillimeter waves that are transmitted from the auxiliary camera 211C and propagates the millimeter waves/submillimeter waves to the control device 5. The control device 5 receives the image signal that is captured by the auxiliary camera 211C and causes the display device 3B to display an image based on the image signal.

According to Modification 3-1 described above, the following effect is achieved in addition to the same effect as that of the above-described third embodiment.

According to Modification 3-1, the waveguide 25 is capable of propagating the millimeter waves/submillimeter waves that are transmitted from the auxiliary camera 211C with which the treatment tool TT1 is provided. This enables an increase in the number of cameras that capture images of an affected site and displays of various images that are captured from different viewpoints.

Other Embodiments

The modes for carrying out the disclosure have been described; however, the disclosure should not be limited to only the above-described first to third embodiments.

In the above-described first to third embodiments, the waveguide 25 is flexible; however, the waveguide 25 is not limited to this. The waveguide 25 need not necessarily be flexible.

In the above-described first to third embodiments, the waveguide 25 is extended to the connector 24; however, the waveguide 25 is not limited to this. The waveguide 25 only need be extended at least to the operation portion 22. When the configuration in which the waveguide 25 is extended to the operation portion 22 is employed, the receiver circuit 51 and the image signal processing circuit 52 may be provided in the operation portion 22. The image signal processing circuit 52 and the control device 5 are connected with, for example, a lead wire.

In the above-described first to third embodiments, the insertion device according to the disclosure is used in the medical fields; however, the use is not limited to this. The insertion device may be used in the industrial fields.

According to the insertion device according to the disclosure, it is possible to overcome the limit of the transfer rate and reduce the diameter of the distal end portion of the insertion portion.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
   an insertion portion configured to be inserted into a subject;
   an imaging unit that includes an imaging element and an optical element and that is arranged at a distal end of the insertion portion, the imaging unit being configured to capture an internal image of the subject to generate an image signal;
   a transmitter that is arranged adjacent to a proximal end side of the imaging unit in the insertion portion, the transmitter being configured to transmit the image signal using millimeter waves or submillimeter waves; and
   a waveguide that is arranged on a proximal end side of the transmitter in the insertion portion and at a position distant from the transmitter with a distal end surface of the waveguide facing the transmitter, the waveguide being configured to propagate the millimeter waves or submillimeter waves;

wherein the insertion portion includes a bendable portion that is provided in part of the insertion portion in a longitudinal direction of the insertion portion and that is bendable, the imaging unit and the transmitter are provided on a distal end side of the bendable portion, and the distal end surface of the waveguide is provided on a proximal end side of the bendable portion.

2. The insertion device according to claim 1, wherein the waveguide is flexible.

3. The insertion device according to claim 2, wherein the waveguide includes a core that is made of a rod-shaped dielectric; and an outer conductor that is provided on an outer circumference of the core and that is formed by braiding filament yarns into a braid.

4. The insertion device according to claim 1, wherein the bendable portion is provided with a transfer path that is made of air or a dielectric and that extends from the transmitter to the distal end surface of the waveguide.

5. The insertion device according to claim 1, wherein the insertion portion includes a flexible tube that is coupled to the proximal end side of the bendable portion and that is flexible, and the waveguide is flexible, is inserted into the flexible tube, and is configured to propagate the image signal toward a proximal end side of the insertion portion.

6. The insertion device according to claim 1, further comprising an operation portion that is coupled to a proximal end side of the insertion portion, the operation portion being configured to receive a user operation, wherein the waveguide is extended at least to the operation portion.

* * * * *